(12) United States Patent
Kadyshevitch et al.

(10) Patent No.: US 6,781,126 B2
(45) Date of Patent: Aug. 24, 2004

(54) AUGER-BASED THIN FILM METROLOGY

(75) Inventors: Alexander Kadyshevitch, Moddieen (IL); Avi Simon, Rehovot (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 10/209,509

(22) Filed: Jul. 30, 2002

(65) Prior Publication Data

US 2003/0146379 A1 Aug. 7, 2003

Related U.S. Application Data

(60) Provisional application No. 60/354,362, filed on Feb. 4, 2002.

(51) Int. Cl.$^7$ ............................. G01N 23/00; G21K 7/00
(52) U.S. Cl. ....................... 250/310; 250/305; 250/307
(58) Field of Search ................................ 250/305, 307, 250/310

(56) References Cited

U.S. PATENT DOCUMENTS 5,981,001 A * 11/1999 Komatsu et al. ............ 427/582
6,399,944 B1 * 6/2002 Vasilyev et al. ............ 250/310

OTHER PUBLICATIONS

L.L. Kamerski, Chapter 4 of Microanalysis of Solids entitled: "Auger Electron Spectroscopy", (Plenum Press, New York, 1994).

Smart–Tool, http://ww.phi.com/, 2002.

Super CMA, http://www.staib–instruments.com/, 2002.

Neidrig, "Film–thickness determination in electron microscopy: the electron backscattering method", Published in Optica Acts 24(6), p. 679, 1997.

C.E. Bryson, et al., "Measurement of carbon film thickness by inelastic electron scatter", May 15, 2000.

F. Schlichting, et al., "Thickness Determination of Ultra–Thin Film Using Backscattered Electron Spectra of a New Toroidal Electrostatic Spectrometer", SCANNING vol. 21 (1999).

* cited by examiner

*Primary Examiner*—John R. Lee
*Assistant Examiner*—Paul M. Gurzo
(74) *Attorney, Agent, or Firm*—Blakely Sokoloff Taylor & Zafman, LLP.

(57) ABSTRACT

Apparatus for analysis of a thin film formed over an underlying layer on a surface of a sample, the thin film including first elements, while the underlying layer includes second elements. The apparatus includes an electron gun, which directs a beam of electrons to impinge on a point on the surface of the sample at which the thin film is formed. An electron detector receives Auger electrons emitted by the first and second elements responsive to the impinging beam of electrons, and to output a signal indicative of a distribution of energies of the emitted electrons. A controller receives the signal and analyzes the distribution of the energies so as to determine a composition of the first elements in the thin film and a thickness of the thin film.

25 Claims, 4 Drawing Sheets

AUGER-BASED THIN FILM METROLOGY

CROSS-REFERENCE TO RELATED APPLICATION

This application claims the benefit of U.S. Provisional Patent Application No. 60/354,362, filed Feb. 4, 2002, which is incorporated herein by reference.

FIELD OF THE INVENTION

The present invention relates generally to semiconductor device manufacturing and process control, and specifically to monitoring the thickness and composition of ultra-thin layers deposited on semiconductor wafers.

BACKGROUND OF THE INVENTION

Auger electron spectroscopy (AES) is a well-known technique for measuring chemical and compositional properties of materials. The principles of AES and its use in various analytical applications are described, for example, by Kazmerski, in Chapter 4 of *Microanalysis of Solids* (Plenum Press, New York, 1994), which is incorporated herein by reference.

AES is based on measuring the energy spectra of characteristic electrons, referred to as Auger electrons, which are emitted from a solid that is irradiated by an energetic ionizing beam, typically an electron beam. The beam causes ionization of atomic core levels in the solid. The resulting core-level vacancy is immediately filled by another electron from a higher energy level in a radiationless process. The energy released by the transition of the electron from the higher level to the core level is transferred to another electron in the same level or close to it, enabling this latter electron—the Auger electron—to escape from the atom. The kinetic energy of the Auger electron is determined by the work function of the atom and the structure of its energy levels.

Because of the nature of the Auger process, every element (except hydrogen and helium) is characterized by a unique Auger spectrum, with well-defined energy peaks. These spectra are well documented in the scientific literature. By analyzing the distribution and amplitudes of the lines in the Auger spectrum of a given material, it is possible to determine the elemental components of the material and their relative concentrations. Analytical systems based on AES are commercially available. For example, the "SMART-Tool," produced by Physical Electronics, Inc. (Eden Prairie, Minne.) uses AES to identify and analyze microscopic defects and contamination on semiconductor wafers and magnetic drive heads.

Auger electrons created by the incident ionizing beam must escape from the sample in order to be detected and analyzed. After the Auger electrons break free of their host atoms, however, they rapidly undergo energy losses due to collisions and other phenomena. In semiconductors and metals, the mean free paths of Auger electrons are typically on the order of 0.4 to 5 nm. Therefore, only Auger electrons created very near the surface of the material under study have a significant probability of escaping and being detected. As a result, AES provides data only on the uppermost surface layers of the material. This feature of AES is clearly advantageous in surface and thin film analysis applications.

SUMMARY OF THE INVENTION

A number of new processes in semiconductor device fabrication involve the formation of ultra-thin surface layers, with thickness in the range of 1 nm or less. For good, consistent device performance, the thickness and composition of such layers must be measured and precisely controlled. In order to maximize yield and correct process errors, the thickness and composition measurements should be made while the wafers are in process, after the ultra-thin layer has been formed, and before the next layer is deposited over it. If the wafer is exposed to ambient air before forming the next layer, however, the desired properties of the ultra-thin layer may be ruined by oxidation and/or water adsorption. The wafer cannot thereafter be returned to the production chamber. There is therefore a need for compact tools that are capable of rapidly and accurately measuring the thickness and composition of ultra-thin layers in the production environment.

In response to this need, preferred embodiments of the present invention provide a fast, inexpensive Auger metrology chamber, which can be integrated with cluster tools used in semiconductor wafer fabrication. The chamber comprises an electron gun, which irradiates a small, selected spot on the wafer surface, and an analyzer, which measures the resultant Auger electron spectrum. The spectrum includes atomic emission peaks both from the ultra-thin layer on the wafer surface and from the underlying layer below it. The relative intensities of the peaks are used to determine both the composition of the ultra-thin layer and its thickness. This information can be used to detect and correct process defects in situ, without ruining the ultra-thin layer by exposing it to ambient air outside the cluster tool.

Although preferred embodiments described herein are directed specifically to fabrication of microelectronic devices on semiconductor wafers, the principles of the present invention may similarly be applied to measuring composition and thickness of ultra-thin layers formed on substrates of other types.

There is therefore provided, in accordance with a preferred embodiment of the present invention, apparatus for analysis of a thin film formed over an underlying layer on a surface of a sample, the thin film including first elements, while the underlying layer includes second elements, the apparatus including:

an electron gun, which is adapted to direct a beam of electrons to impinge on a point on the surface of the sample at which the thin film is formed;

an electron detector, which is adapted to receive Auger electrons emitted by the first and second elements responsive to the impinging beam of electrons, and to output a signal indicative of a distribution of energies of the emitted electrons; and a controller, which is coupled to receive the signal and to analyze the distribution of the energies so as to determine a composition of the first elements in the thin film and a thickness of the thin film.

Preferably, the controller is adapted to find first and second peaks in the distribution of the energies corresponding respectively to the Auger electrons emitted by the first and second elements, the peaks having respective amplitudes, and to analyze the amplitudes of the first second peaks in order to determine the composition and thickness of the thin film. Most preferably, the controller is adapted to compare the amplitudes of the second peaks to the amplitudes of the first peaks in order to estimate an attenuation of the Auger electrons emitted by the second elements, so as to determine thereby the thickness of the thin film. Additionally or alternatively, the controller is adapted to compare the amplitudes of the first peaks one to another so as to determine the composition of the thin film.

There is also provided, in accordance with a preferred embodiment of the present invention, a cluster tool for producing microelectronic devices, including:

a deposition station, which is adapted to form a thin film including first elements over an underlying layer on a surface of a semiconductor wafer, the underlying layer including second elements;

a testing station, including:

an electron gun, which is adapted to direct a beam of electrons to impinge on a point on the surface of wafer at which the thin film is formed;

an electron detector, which is adapted to receive Auger electrons emitted by the first and second elements responsive to the impinging beam of electrons, and to output a signal indicative of a distribution of energies of the emitted electrons; and a controller, which is coupled to receive the signal and to analyze the distribution of the energies so as to determine a composition of the first elements in the thin film and a thickness of the thin film, and to adjust an operating parameter of the deposition station responsive to at least one of the composition and the thickness.

Preferably, the tool includes a robot, which is adapted to transfer the wafer from the deposition station to the testing station, while the wafer is maintained in a vacuum.

In a preferred embodiment, the thin film formed by the deposition station includes a gate dielectric layer. In another preferred embodiment, the deposition station is adapted to form the thin film by atomic layer deposition. Preferably, the thin film formed by atomic layer deposition includes a conductive barrier layer formed in preparation for deposition of a metal seed on the surface.

Preferably, the thickness of the thin film is less than 50 nm, more preferably less than 5 nm, and most preferably less than 1 nm.

There is additionally provided, in accordance with a preferred embodiment of the present invention, a method for production testing, including:

receiving a sample including a thin film formed over an underlying layer on a surface of the sample, the thin film including first elements, while the underlying layer includes second elements;

directing an electron beam to impinge on a point on the surface of the sample at which the thin film is formed;

receiving Auger electrons emitted by the first and second elements responsive to the impinging beam of electrons; and analyzing a distribution of energies of the emitted electrons so as to determine a composition of the first elements in the thin film and a thickness of the thin film.

The present invention will be more fully understood from the following detailed description of the preferred embodiments thereof, taken together with the drawings in which:

DETAILED DESCRIPTION OF PREFERRED EMBODIMENTS

Figure 1:
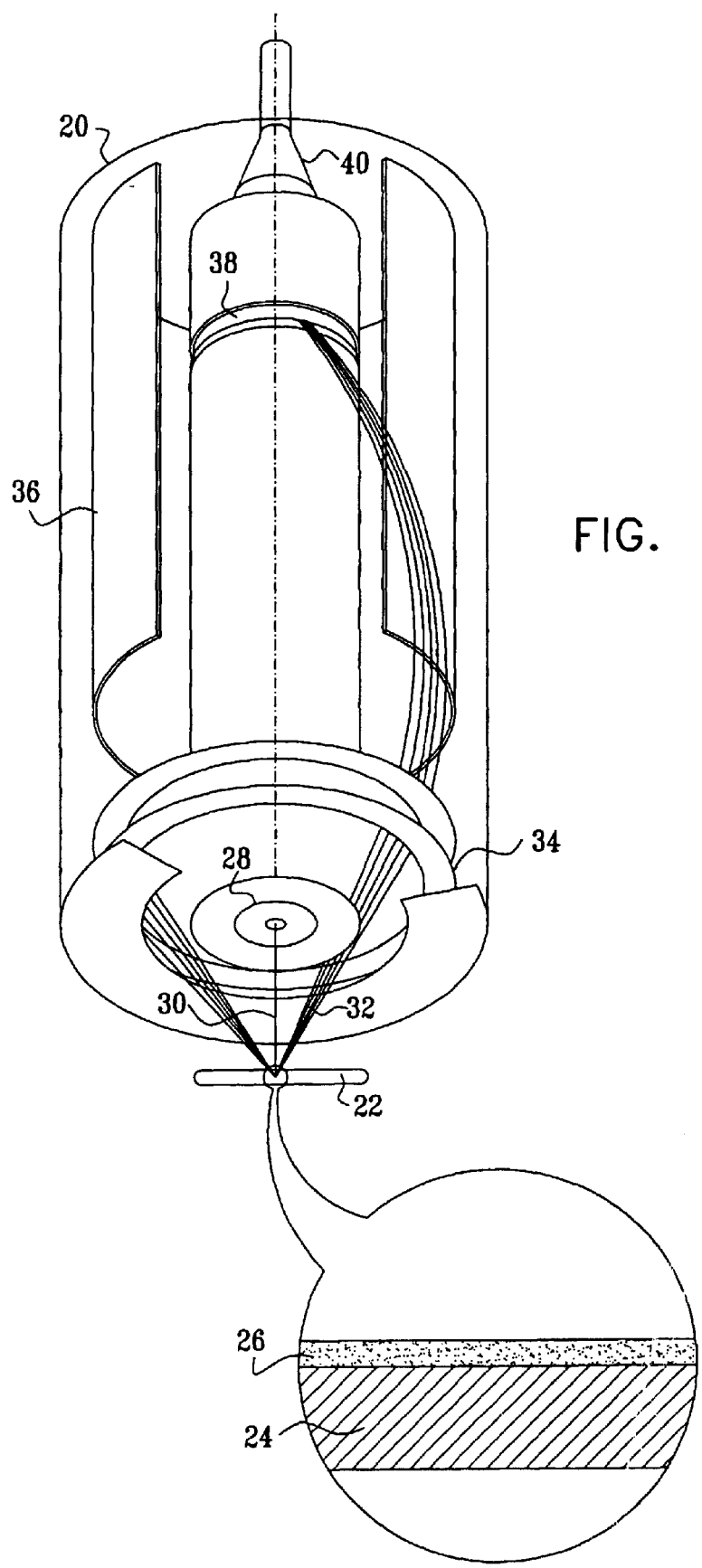
FIG. 1 is a schematic, pictorial, partially cutaway view of an Auger analyzer for thin film layers, in accordance with a preferred embodiment of the present invention.

FIG. 1 is a schematic, pictorial, partly cutaway view of an Auger analysis tool 20, for use in a thin film metrology chamber, in accordance with a preferred embodiment of the present invention. Analyzer 20 is configured to detect Auger electrons emitted from a semiconductor wafer 22. The wafer comprises an ultra-thin film 26, which is formed over an underlying layer 24. Typically, thin film 26 is less than 50 nm thick. Analyzer 20 is most advantageously used, however, for layers that are less than 5 nm thick, and it may even be used for layers less than 1 nm thick. Some examples of such ultra-thin layers used in modern semiconductor devices are described hereinbelow.

Auger tool 20 is configured as a cylindrical mirror analyzer (CMA), as is known in the analytical art. A CMA of this sort, known as "SUPERCMA" is produced by Staib Instruments GmbH (Munich, Germany). Further information regarding this CMA is available at www.staibinstruments.com, from which FIG. 1 is adapted. Alternatively, other types of electron analyzers may be used for Auger analysis, such as a Cylindrical Sector Analyzer (CSA) with a channeltron detector. A CSA of this sort is produced by Focus GmbH (Hünstetten-Görsroth, Germany).

Tool 20 comprises a coaxial electron gun 28, which directs a beam 30 of electrons toward a point on the surface of wafer 22. The electron beam is focused to a tight spot on the wafer surface, with a spot diameter that is preferably no more than about 10–30 $\mu$m in diameter. The position of the beam focus is preferably sufficient stable so that it varies by no more than 5 $\mu$m over a measurement period. The tight focus of the electron beam is useful because it allows measurement of film 26 at precise locations on the wafer surface, such as the location of a particular gate of which film 26 is a part. The electron energy of the gun is preferably in the range of 1–15 keV, with narrow energy spread (most preferably <1 eV) and beam current in the range of 1 nA to 1 $\mu$A.

Electrons scattered from wafer 22 are collected through a retarding lens 34, which enables a cylindrical mirror 36 to focus the electrons 32 into an exit slit 38. These electrons are received by a detector 40, preferably an electron counting detector, as is known in the art. The detector provides a count of the number of electrons emitted from wafer 22 as a function of electron energy. The electrons scattered from the wafer are preferably collected over an energy range of at least 0–2500 eV, with energy resolution of 2% or better and high energy calibration stability. For high signal/noise ratio and throughput, tool 20 is preferably designed to capture electrons from the wafer over an angular range of at least 30°, with collection efficiency (relative to $2\pi$ of solid angle) of at least 5%. For this purpose, it is also desirable that detector 40 comprise multiple parallel acquisition channels.

Figure 2:
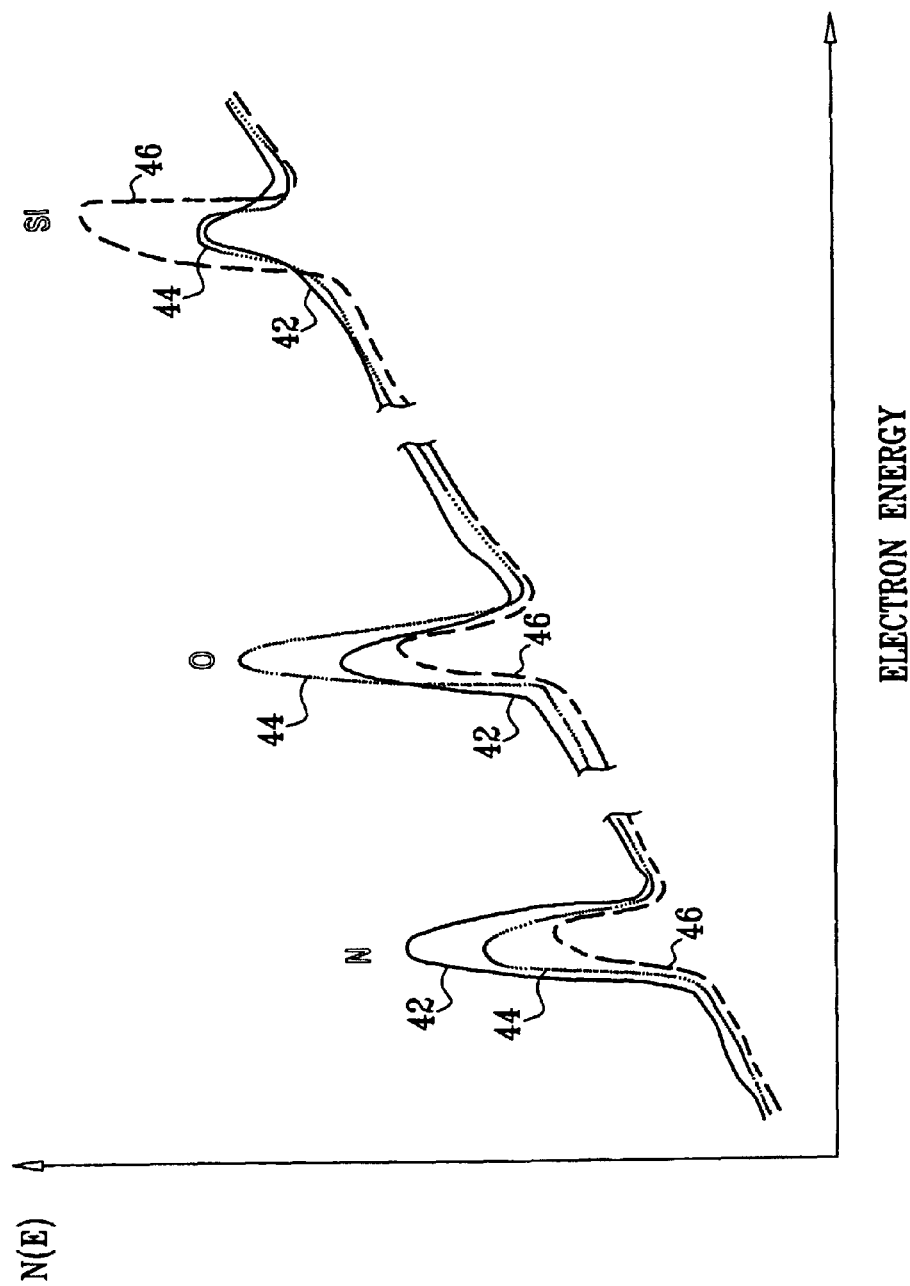
FIG. 2 is a schematic plot of Auger spectra obtained from thin film layers of varying thickness, in accordance with a preferred embodiment of the present invention.

FIG. 2 is a schematic plot of Auger spectra obtained from silicon oxinitride layers of varying thickness and composition, which are formed over a silicon substrate. These spectra show the number of electrons emitted N(E), as a function of the electron energy. They include three peaks, corresponding to the following characteristic Auger electron emission lines of nitrogen (N), oxygen (O) and silicon (Si):

N—KLL line: 380 eV

O—KLL line: 507 eV

Si—KLL Line: 1615 eV.

Typically, the Auger spectrum includes multiple Auger lines for each element, corresponding to different inner-level electron transitions. Only one line per element is shown here, however, for the sake of simplicity and clarity. Analyzer 20 also collects back-scattered electrons, which give rise to the smoothly-varying background below the Auger peaks shown in the figure.

FIG. 2 includes spectra taken from three different films:

A first spectrum 42, with a high nitrogen/oxygen ratio in film 26.

A second spectrum 44, with a lower nitrogen/oxygen ratio.

A third spectrum 46, in which film 26 is thinner, relative to the first two spectra.

It will be observed that the relative amplitudes of the N and O peaks, corresponding to the composition of the thin film layer, reflect the relative concentrations of the elements in the layer. Furthermore, as film 26 is made thicker, the attenuation of Auger electrons emitted from the silicon in underlying layer 24 leads to a reduction in the amplitude of the Si peak. Preferably, for each type of thin film to be evaluated by analyzer 20, calibration measurements of the Auger spectrum are made using a number of different films of known thickness and composition. Based on these calibration measurements, the thickness and composition of other films of the same type can be determined based on the amplitudes of the peaks in their Auger spectra. This method is sufficiently accurate to give readings of the thickness of film 26 to a precision of about 0.01 nm.

Figure 3:
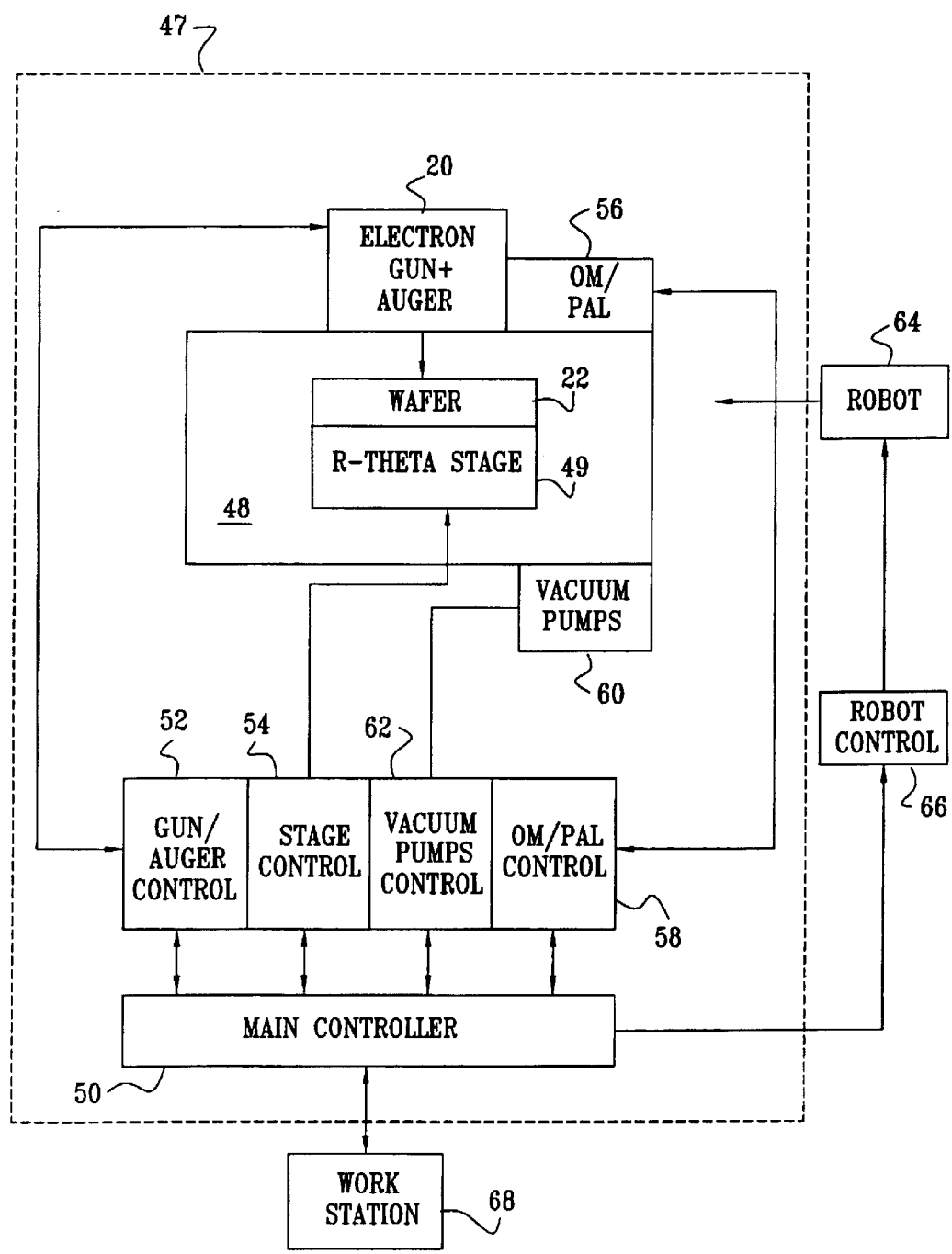
FIG. 3 is a block diagram that schematically illustrates apparatus for thin film metrology, in accordance with a preferred embodiment of the present invention.

FIG. 3 is a block diagram that schematically illustrates a station 47 for Auger metrology of wafer 22, in accordance with a preferred embodiment of the present invention. Station 47 comprises a chamber 48, containing a motion stage 49 on which wafer 22 is placed during measurement. Auger analyzer 20, as shown in FIG. 1, directs its electron beam at wafer 22, and receives the Auger and backscattered electrons emitted from the wafer.

Stage 49 positions wafer 22 so that a desired point on the wafer is properly located in the beam of electron gun 28. For example, the electron beam may be aimed at the location of a particular gate in which film 26 has been formed. Alternatively, the beam may be directed at a special test location on wafer 22, which is preferably located in a scribe line, between two dice. Given the large characteristic size (30 $\mu$m) of the pattern and of the electron beam, positioning resolution of about ±5 $\mu$m is generally sufficient. For simplicity and economy of space, stage 49 preferably comprises an R-theta (translation/rotation) stage. Alternatively or additionally, the stage may provide X-Y translation, or analyzer 20 may be translated over wafer 22. Preferably, stage 49 positions the wafer (or the analyzer is translated) so that several locations are irradiated by the electron beam in succession. The Auger spectrum is measured at each location, in order to ensure that uniformity of film 26 is maintained over the entire wafer.

Optionally, station 47 also comprises an ammeter (not shown), coupled to wafer 22, for measuring specimen currents generated in the wafer due to irradiation by electron gun 28. The use of specimen current measurements in monitoring production steps applied to semiconductor wafers is described in a U.S. provisional patent application serial No. 60/354361 entitled, "Monitoring of Contact Hole Production," filed Apr. 2, 2002, which is assigned to the assignee of the present patent application and whose disclosure is incorporated herein by reference.

The positioning and operation of analyzer 20 and stage 49 are controlled by a main controller 50, via a gun/Auger control unit 52 and a stage control unit 54. Typically, a pre-alignment unit based on a low-resolution optical microscope (OM/PAL) 56 is used by controller 50, via an OM/PAL control unit 58, to align the electron beam with the point on the wafer that is to be tested. For this purpose, the microscope preferably has a resolution of 3–4 $\mu$m over a 1×1 mm field of view. Suitable microscopes for this purpose are made, for example, by Optem (Fairport, N.Y.).

During operation, a vacuum is maintained in chamber 48 by a vacuum pump 60, which is also controlled and monitored by controller 50, via a vacuum control unit 62. Although AES systems known in the art are typically designed to operate in an ultra-high vacuum (UHV) of $10^{-9}$ to $10^{-10}$ torr, the inventor has found that a vacuum of $10^{-6}$ to $10^{-7}$ torr gives satisfactory results for the types of thin film measurements described in the present patent application, as long as the level of organic vapors in chamber 48 is kept at UHV levels. This feature of the present invention allows chamber 47 to be integrated with other chambers in a cluster tool, as described below. If a vacuum of $10^{-9}$–$10^{-10}$ torr were required, such integration would be much more difficult to accomplish.

A robot 64 inserts wafers into chamber 42 and removes them from the chamber. Controller 50 communicates with the robot via a robot control unit 66. Robot 64 is preferably used to transfer wafers to and from other stations in a cluster tool, as shown below in FIG. 4.

After positioning stage 49 and operating analyzer 20, controller 50 receives the electron counts collected by detector 40 (FIG. 1). The controller analyzes the spectra of electron counts against energy (as shown in FIG. 2), and compares the measured peak amplitudes to calibration data in order to determine the thickness and composition of film 26. Controller 50 may also use the backscattered (non-Auger) electron signal in determining the thickness of certain films, as described, for example, by Niedrig, in "Film-Thickness Determination in Electron Microscopy: The Electron Backscattering Method," published in *Optica Acta* 24(6), p. 679 (1977), which is incorporated herein by reference.

If the controller determines that the film thickness or composition is outside a predetermined tolerance range, it preferably interrupts the production process and notifies a system operator via a user workstation 68. The operator evaluates the test results and then invokes whatever corrective action may be necessary. This action may include, for example, continuing the deposition process on the current wafer if film 26 is too thin, and/or adjusting production parameters to correct the thickness and composition of films to be formed on subsequent wafers.

Figure 4:
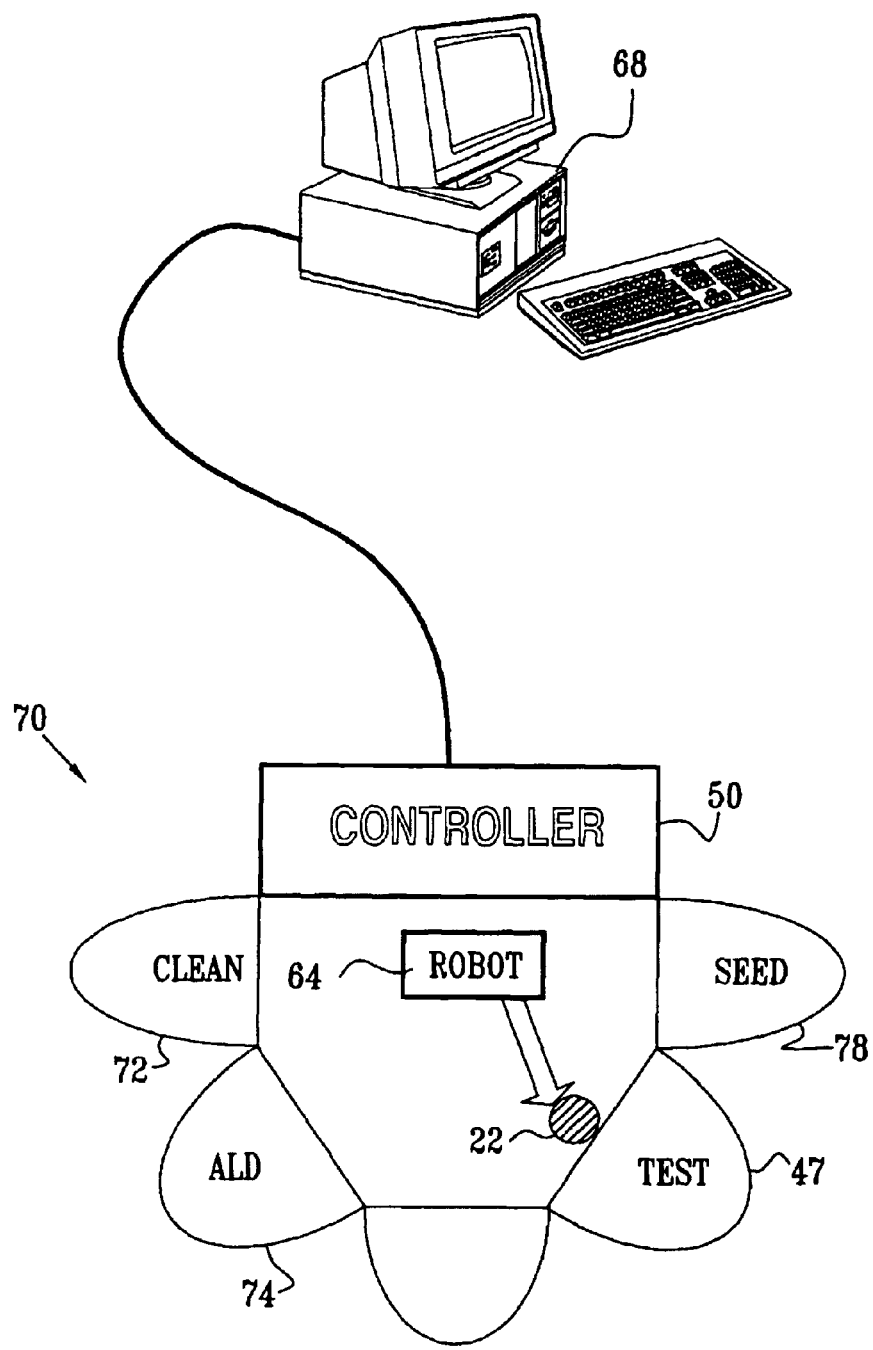
FIG. 4 is a schematic top view of a cluster tool that includes a thin film metrology station, in accordance with a preferred embodiment of the present invention.

FIG. 4 is a schematic top view of a cluster tool 70 in which test station 47 is integrated, in accordance with a preferred embodiment of the present invention. This integration is made possible by the small size and simplicity of the components of test station 47, and by the fact that the test station does not require UHV to operate. Other methods of ultra-thin film metrology, such as X-ray or optical methods, cannot easily be made to fit into the cluster tool framework or, if adapted to work in this framework, suffer from shortcomings of poor resolution and/or low throughput. Optical methods based on ellipsometry may be satisfactory for some purposes, but only if the composition of film 26 is precisely determined by some other method. The reason for this limitation is that the ellipsometric measurement is sensitive to the refractive index of the film, which varies with composition. Therefore, ellipsometry can be used for extremely thin films to deduce only a product of thickness and refractive index.

In the embodiment pictured in FIG. 4, robot 64 receives wafer 22 after underlying layer 24 has been deposited on the wafer and has been prepared for a metal seed layer above it. This embodiment and the corresponding configuration of tool 70 are chosen by way of example, and other processes and configurations may similarly be implemented. Since the interior of tool 70 is evacuated, robot 64 is able to transfer wafer 22 from chamber to chamber without exposing the wafer to ambient air. Optionally, the wafer is first cleaned in a cleaning station 72, and is then inserted in an atomic layer deposition (ALD) station 74. The purpose of this step is to form a barrier layer over the underlying dielectric or semiconductor layer 24 before metal seeding, in order to prevent subsequent diffusion of metal into the underlying layer. The barrier layer typically comprises TaN, TiS or SrS, or another material known in the art.

After film 26 has been deposited on wafer 22 to serve as the barrier layer, the wafer is passed to test station 47. In station 47, the Auger spectrum of electrons emitted from wafer 22 is measured, and the results are evaluated by controller 50, as described above, in order to determine the thickness and composition of the barrier layer. A TaN barrier layer, for example, should have a thickness set precisely to a value between about 0.5 and 3 nm. If the thickness and composition of film 26 are found to be within a predetermined tolerance range (preferably to within about ±0.05 nm) of the nominal value, the barrier layer is deemed to be acceptable. Robot 64 then moves wafer 22 into a seeding station 78 for application of a copper seed over the barrier layer. The copper seed layer is preferably about 5 nm thick. If desired, the Auger measurement in test station 47 may be repeated after the seeding step to verify the thickness of the copper seed layer, as well.

On the other hand, if the barrier layer is found to be too thin, robot 64 may be instructed to return the wafer to ALD station 74 for further deposition, to be followed by re-test in station 47. Alternatively or additionally, workstation 68 may be used to adjust the process parameters in order to correct any process deviations.

As another example, tool 70 may be adapted for growing gate dielectric layers between the gate and overlying conductor in CMOS transistors formed on wafer 22. Typically, the gate dielectric comprises a thin layer of silicon oxinitride, between about 0.5 and 2 nm thick, which is formed by plasma nitridation of thermally-grown oxide. For consistent control of the transistors' electrical parameters, the dielectric layer thickness is preferably monitored using test station 47, so that the thickness of the layer is within about ±0.01 nm of specification. The nitrogen concentration is carefully controlled, as well, preferably to within about ±0.75%. Polysilicon is then deposited over the dielectric layer using one of the stations of tool 70, before the wafer is removed to ambient air.

In addition to these examples, AES in station 47 may similarly be used for stoichiometric analysis of layers of other types, as well as for measurement and control of contaminant levels. Station 47 may also be adapted for other types of measurements, such as measurement of specimen current for contact hole monitoring, as noted above, and X-ray spectrometry for measurement of implant doses. Other possible modifications will be apparent to those skilled in the art.

Although preferred embodiments described herein are directed specifically to fabrication of microelectronic devices on semiconductor wafer 22, the principles of the present invention may similarly be applied to measuring composition and thickness of ultra-thin layers formed on substrates of other types. It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A cluster tool for producing microelectronic devices, comprising:

a deposition station, which is adapted to form a thin film comprising first elements over an underlying layer on a surface of a semiconductor wafer, the underlying layer comprising second elements;

a testing station, comprising:

an electron gun, which is adapted to direct a beam of electrons to impinge on a point on the surface of wafer at which the thin film is formed;

an electron detector, which is adapted to receive Auger electrons emitted by the first and second elements responsive to the impinging beam of electrons, and to output a signal indicative of a distribution of energies of the emitted electrons; and a controller, which is coupled to receive the signal and to analyze the distribution of the energies so as to determine a composition of the first elements in the thin film and a thickness of the thin film, and to adjust an operating parameter of the deposition station responsive to at least one of the composition and the thickness.

2. A tool according to claim 1, and comprising a robot, which is adapted to transfer the wafer from the deposition station to the testing station, while the wafer is maintained in a vacuum.

3. A tool according to claim 1, wherein the thin film formed by the deposition station comprises a gate dielectric layer.

4. A tool according to claim 1, wherein the deposition station is adapted to form the thin film by atomic layer deposition.

5. A tool according to claim 4, wherein the thin film formed by atomic layer deposition comprises a barrier layer formed in preparation for deposition of a metal seed on the surface.

6. A tool according to claim 1, wherein the thickness of the thin film is less than 50 nm.

7. A tool according to claim 6, wherein the thickness of the thin film is less than 5 nm.

8. A tool according to claim 7, wherein the thickness of the thin film is less than 1 nm.

9. A tool according to claim 1, wherein the controller is adapted to find first and second peaks in the distribution of the energies corresponding respectively to the Auger electrons emitted by the first and second elements, the peaks having respective amplitudes, and to analyze the amplitudes of the first second peaks in order to determine the composition and thickness of the thin film.

10. A tool according to claim 9, wherein the controller is adapted to compare the amplitudes of the second peaks to the amplitudes of the first peaks in order to estimate an attenuation of the Auger electrons emitted by the second elements, so as to determine thereby the thickness of the thin film.

11. A tool according to claim 9, wherein the controller is adapted to compare the amplitudes of the first peaks one to another so as to determine the composition of the thin film.

12. A method for producing and testing microelectronic devices, the method comprising:

receiving a sample from a deposition station, the sample comprising a thin film formed over an underlying layer on a surface of the sample, the thin film comprising first elements, while the underlying layer comprises second elements;

directing an electron beam to impinge on a point on the surface of the sample at which the thin film is formed;

receiving Auger electrons emitted by the first elements and the second elements responsive to the electron beam;

analyzing a distribution of energies of the Auger electrons so as to determine a composition of the thin film and a thickness of the thin film; and adjusting an operating parameter of the deposition station responsive to at least one of the determined composition and thickness.

13. A method according to claim 12, wherein the sample comprises a semiconductor wafer, and wherein receiving the sample comprises forming the thin film on the wafer.

14. A method according to claim 13, wherein forming the thin film comprises depositing the thin film on the wafer in a deposition chamber, and wherein receiving the sample further comprises transferring the wafer from the deposition station to a testing chamber while the wafer is maintained in a vacuum, wherein the steps of directing the electron beam and receiving the Auger electrons are performed in the testing chamber.

15. A method according to claim 13, wherein forming the thin film comprises depositing gate dielectric layer on the wafer.

16. A method according to claim 13, wherein forming the thin film comprises applying atomic layer deposition to the wafer.

17. A method according to claim 16, wherein applying the atomic layer deposition comprises forming a barrier layer in preparation for deposition of a metal seed on the wafer.

18. A method according to claim 13, wherein the thickness of the thin film is less than 50 nm.

19. A method according to claim 18, wherein the thickness of the thin film is less than 5 nm.

20. A method according to claim 19, wherein the thickness of the thin film is less than 1 nm.

21. A method according to claim 12, wherein analyzing the distribution comprises finding first and second peaks in the distribution of the energies corresponding respectively to the Auger electrons emitted by the first and the second elements, the peaks having respective amplitudes, and analyzing the amplitudes of the first second peaks in order to determine the composition and thickness of the thin film.

22. A method according to claim 21, wherein analyzing the amplitudes comprises comparing the amplitudes of the second peaks to the amplitudes of the first peaks in order to estimate an attenuation of the Auger electrons emitted by the second elements, so as to determine thereby the thickness of the thin film.

23. A method according to claim 12, wherein analyzing the distribution comprises comparing the amplitudes of the first peaks one to another so as to determine the composition of the thin film.

24. A method according to claim 12, wherein receiving the sample comprises receiving the sample from the deposition station that further comprises a means for plasma nitridation of thermally grown oxide.

25. A method according to claim 12, wherein adjusting an operating parameter of the deposition station comprises adjusting at least one of film thickness, deposition time, pressure and chamber vapor concentrations.

* * * * *